United States Patent [19]

English et al.

[11] Patent Number: 4,804,691

[45] Date of Patent: Feb. 14, 1989

[54] METHOD FOR MAKING A BIODEGRADABLE ADHESIVE FOR SOFT LIVING TISSUE

[75] Inventors: James P. English, Birmingham, Ala.; Gerald W. McNeely, Spartanburg, S.C.; Richard L. Dunn, Birmingham, Ala.

[73] Assignee: Richards Medical Company, Memphis, Tenn.

[21] Appl. No.: 90,861

[22] Filed: Aug. 28, 1987

[51] Int. Cl.$^4$ .............................................. C08G 18/30
[52] U.S. Cl. ..................................... 523/118; 528/54; 528/55; 528/81; 528/83; 528/905
[58] Field of Search ................... 523/118; 528/54, 55, 528/81, 83, 905

[56] References Cited

U.S. PATENT DOCUMENTS

| | | |
|---|---|---|
| 3,221,745 | 12/1965 | Coover, Jr. et al. |
| 3,463,158 | 8/1969 | Schmitt et al. |
| 3,867,190 | 2/1975 | Schmitt et al. |
| 4,057,535 | 11/1977 | Lipatova et al. |
| 4,243,775 | 1/1981 | Rosensaft et al. |
| 4,273,920 | 6/1981 | Nevin. |
| 4,539,981 | 9/1985 | Tunc. |
| 4,595,713 | 6/1986 | St. John. |

OTHER PUBLICATIONS

Stephen C. Weber, MD, and Michael W. Chapman, MD, "Adhesives in Orthopaedic Surgery", Clinical Orthopaedics and Related Research, No. 191, Dec., 1984.

Karl H. Siedentop, MD, David M. Harris, PhD, and Ben Sanchez, MD, "Autologous Fibrin Tissue Adhesive", Laryngoscope 95, Sep. 1985.

Karl H. Siedentop, MD, David M. Harris, PhD, and Dennis F. Weber, D.D.S., "Fibrin Tissue Adhesive and Glass Ceramic Strut for Ossicular Chain Replacement", The American Journal of Otology, Vol. 6, No. 3, May, 1985.

Marvin H. Meyers, MD, and Michael Herron, D.V.M., "A Fibrin Adhesive Seal for Repair of Osteochondral Fracture Fragments", Clinical Orthopaedics and Related Research, No. 182, Jan.-Feb., 1984.

Michael Evan Sachs, MD, "Enbucrilate as Cartilage Adhesive in Augmentation Rhinoplasty", Arch Olotaryngol, vol. 111, Jun. 1985.

"Human Super Glue Cited for Microperforations", Ocular Surgery News, Jul. 15, 1985, author unknown.

Max L. Ronis, MD, John D. Harwick, MD, Romona Fung, MD, and Michael Dellavecchia, MD, "Review of Cyanoacrylate Tissue Glues with Emphasis on Their Otorhinolaryngological Applications", Laryngoscope 94, Feb. 1984.

M. C. Harper, "Viscous Isoamyl 2-Cyanoacrylate as an Osseous Adhesive in the Repair of Osteochondral Fractures", Orthopaedic Research Society, 1985.

Primary Examiner—John Kight
Assistant Examiner—Sam A. Acquah
Attorney, Agent, or Firm—Kirkpatrick & Lockhart

[57] ABSTRACT

A method for making an adhesive for use in joining soft living tissue including the steps of preparing a hydroxyl-terminated polyester by reacting a biodegradable monomer with a polyhydroxy polymerization initiator in the presence of an amount up to about 2.0 weight percent of a catalyst, and then preparing a diisocyanate-terminated prepolymer adhesive by reacting about 24 to 92 weight percent of the hydroxy-terminated polyester with about 8 to 76 weight percent excess aromatic diisocyante. The polyester and the diisocyanate are preferably dissolved in an organic solvent prior to the mixture thereof in a ratio of solids to solvent of about 60:40. The polyester is a polymer or copolymer of lactide, glycolide or ϵ-caprolactone. The initiator is ethylene glycol, diethylene glycol, pentaerythritol or 1,1,1-tris (hydroxymethyl) ethane. The catalyst is stannous octoate, a zinc compound, an aliphatic tertiary amine, dibutyltin diacetate or 1,4-diazabicyclo [2,2,2] octane.

21 Claims, No Drawings

METHOD FOR MAKING A BIODEGRADABLE ADHESIVE FOR SOFT LIVING TISSUE

BACKGROUND OF THE INVENTION

1. Field of the Invention

The present invention relates to medical adhesives and more particularly, to biodegradable adhesives for connecting soft tissue.

2. Description of the Prior Art

Typically, sutures are used to close incisions in soft tissue. There are, however, complications associated with the use of sutures. For example, tissue incompatibility with sutures often causes fistulas and granulomas. Even necroses can result if sutures restrict blood supply. Sutures also tend to cut through weak parenchymatous tissue and weak, poorly vascularized tissue. In microsurgery, the use of sutures requires special skills and time.

Researchers have, for some time, investigated the use of soft tissue adhesives. The major developments to date have primarily been cyanoacrylate adhesives, fibrin adhesives and gelatin/resorcinol/formaldehyde adhesives.

Cyanoacrylate adhesives were developed in 1959 and were first patented as tissue adhesives in 1973, U.S. Pat. No. 3,759,264. A variety of 2-cyanoacrylate esters can be synthesized by varying the length of the alkyl chain. Although the cyanoacrylates have demonstrated tremendous bonding strength, the degradation products, formaldehyde and alkyl cyanoacetate, cause tissue irritation. Methyl and ethyl cyanoacrylates biodegrade to produce high concentrations of toxic degradation products.

Fibrin adhesive systems are the only natural adhesive system now available. They are essentially two component systems comprised of concentrated human fibrinogen and thrombin and calcium chloride which coagulate when mixed. The fibrin adhesive systems are preferable to cyanoacrylate adhesives because they do not induce toxic or inflammatory responses. However, because the fibrinogen component is manufactured from pooled human blood, there is potential for possible immune reactions or transferral of infection, such as viral hepatitis "B" or human immunodeficiency virus.

Polyurethanes have also been investigated as tissue adhesives. Recent work with castor oil/isocyanate prepolymers of polyurethane indicates that the reactivity of these systems is somewhat slow. The reactivity was shown to increase by the synthesis and use of tetrafluoro 1,3-phenylene diisocyanate, but the adhesion is unsatisfactory compared to that of the cyanoacrylates. The polyurethane systems may also suffer from toxicity problems. These systems contain toxic monomeric diisocyanates, some of which can diffuse away from the reaction site before the reaction occurs. These systems also contain other noxious substances, such as pyridine and tetrahydrofuran. Such conventional polyurethanes are not biodegradable and are believed to act as a barrier to the regeneration of natural tissue.

Poly(methyl methacrylate) cement (PMMA) has been used in dentistry for some time and, more recently, in orthopaedic surgery. PMMA reportedly gives results that frequently do not hold up.

The proteinaceous gelatin/resorcinol/formaldehyde adhesive systems have been widely investigated. Studies to date have been favorable. This system is thought to cross-link with the tissue by condensation of phenolic residues with formaldehyde.

Lipatova et al. U.S. Pat. No. 4,057,535 describes an adhesive for gluing soft tissue comprised of aromatic diisocyanate (from 1 to 50 wt. %), 2, 4, 6-tris (dimethylaminomethyl) phenol (from 0.1 to 20 wt. %) and macrodiisocyanate of the general formula

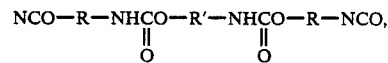

where R is an aromatic diisocyanate radical and R' is a polyether or polyester radical (from 98.9 to 30 wt. %). The Lipatova adhesive biodegrades to ethylene glycol and a diester, neither of which have a normal metabolic function.

There are a number of polymers and copolymers of lactic acid and glycolic acid reported. The advantage of utilizing these copolymers is the fact that the hydrolysis products are constituents in normal metabolic pathways and, thus, are nontoxic. Schmitt et al. U.S. Pat. Nos. 3,463,158 and 3,867,190 describe applications for polyglycolic acid. Nevin U.S. Pat. No. 4,273,920 describes a process for making lactic-glycolic copolymers having molecular weights of about 6000 to about 35,000. Rosensaft et al. U.S. Pat. No. 4,243,775 describes a method for manufacturing surgical articles, such as sutures, from an absorbable copolymer of a glycolide monomer and a cyclic ester monomer made from lactide or selected from the group consisting of lactones, oxalates or carbonates. Tunc U.S. Pat. No. 4,539,981 describes an absorbable bone fixation device made from a high molecular weight polymer of L(-) lactide.

St. John U.S. Pat. No. 4,595,713 describes a medical putty for tissue augmentation comprising a copolymer of a major amount of epsilon caprolactone (60 to 95 wt. %) and a minor amount of lactide (40 to 5 wt. %). Depending upon the application, other components, such as osteogenic material or chopped carbon fiber, may also be included.

Based on research conducted to date, it is believed that no single adhesive is likely to be suited for all types of surgery. Several features of adhesives for soft biological tissue appear to be important. Primarily, the adhesive should be strong enough to hold the wound tissue together until natural tissue regeneration can occur. The adhesive material should be biodegradable and the degradation products should ideally be utilizable in the normal metabolic pathways of the recipient.

It is an object of the present invention to provide an adhesive, and a method for making such an adhesive, for use in augmenting sutures to hold soft biological tissue. It is a further object of the present invention to provide such an adhesive that is itself nontoxic and that yields nontoxic degradation products.

SUMMARY OF THE INVENTION

The present invention provides an adhesive and a method for making such an adhesive which is suited for use in joining soft living tissues, and is particularly well suited for augmenting sutures to join such tissue. The adhesive is comprised of a multifunctional resorbable polyester backbone having diisocyanate end groups wherein the polyester backbone is selected from the group consisting of polymers and copolymers of lactide, glycolide and ε-caprolactone. The polyester portion has a theoretical molecular weight in the range of about 500 to 10,000.

The method for making the adhesive includes the steps of preparing a hydroxyl-terminated polyester by reacting a biodegradable monomer with a polyhydroxy polymerization initiator in the presence of a catalyst and preparing a diisocyanate-terminated prepolymer adhesive by reacting the hydroxyl-terminated polyester with excess aromatic diisocyanate. Prior to reacting the aromatic diisocyanate with the hydroxyl-terminated polyester, each is preferably dissolved in an organic solvent, such as ethyl acetate or dichloromethane. The solvent is removed after stirring to yield the prepolymer adhesive.

The monomer is selected from the group consisting of lactide, glycolide, ε-caprolactone and any combination thereof.

The initiator is selected from the group consisting of ethylene glycol, diethylene glycol, 1,1,1-tris (hydroxymethyl) ethane and pentaerythritol. The catalyst is selected from the group consisting of stannous octoate, zinc compounds, aliphatic tertiary amines, 1,4-diazabicyclo [2,2,2]octane and dibutyltin diacetate. The aromatic diisocyanate may be toluene diisocyanate or methylene-bis-phenyl diisocyanate.

The catalyst is added in an amount up to about 2.0 weight percent. The aromatic diisocyanate is added in an amount from about 8 to 76 weight percent and the hydroxyl-terminated polyester is added in an amount from about 24 to 92 weight percent.

When the prepolymer adhesive is applied to soft tissue, it is hydrolyzed by the moisture on the tissue to promote chain growth and cross linking to effect bonding to the tissue.

DETAILED DESCRIPTION OF THE PREFERRED EMBODIMENTS

The adhesive of the present invention can be a single-component or a two-component system. The adhesive is synthesized according to the following procedure. A biodegradable monomer is reacted with a polyhydroxy polymerization initiator in the presence of a catalyst to produce a hydroxyl-terminated polyester. One example of the ring opening polymerization reaction may proceed as follows:

Reaction Sequence I

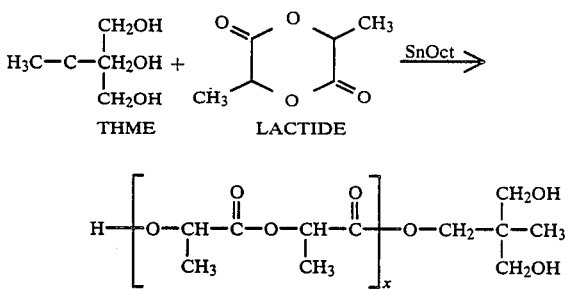

HYDROXYL-TERMINATED (POLYLACTIDE)

In the sequence shown, the initiator is 1,1,1-tris (hydroxymethyl) ethane (THME), the monomer is lactide, and the catalyst is stannous octoate.

The mechanism can be modified by varying the multifunctional initiator to give a variety of linear and branched OH-terminated materials. The molecular-weight range of the prepolymer adhesive can be controlled by the type and quantity of initiator present. The monomer and initiator can be varied to form hydroxyl-terminated polymers and copolymers with varying levels of terminal hydroxyl content. The prepolymer may be any combination of lactide, glycolide and ε-caprolactone. Preferred examples are poly(DL-lactide), and 50:50 poly (DL-lactide)/ε-caprolactone. The initiator can be any suitable polyhydroxy compound, such as ethylene or diethylene glycol or pentaerythritol. The catalyst can be a zinc compound, such as zinc acetate; an aliphatic tertiary amine, such as N-methyl morpholine, triethylamine and triethylene diamine (DABCO); an aromatic tertiary amine, such as pyrazine, 1,4-diazabicyclo [2,2,2]octane; stannous octoate or dibutyltin diacetate. The preferred catalysts are stannous octoate, dibutyltin diacetate and 2,4-diazabicyclo [2,2,2]octane.

Once the hydroxyl-terminated polyester has been prepared, the final tissue adhesive can be formed by either the single component method or the two component method. For the single component adhesive, the hydroxyl-terminated polyester obtained from the first reaction step is reacted with excess diisocyanate to form an isocyanate-terminated prepolymer adhesive according to the following sequence:

REACTION SEQUENCE 2

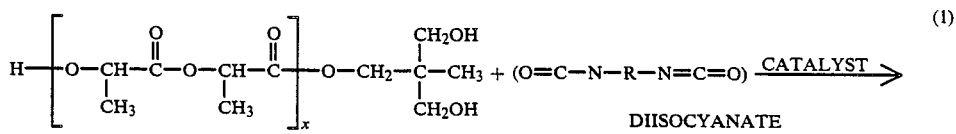

(1)

-continued
REACTION SEQUENCE 2
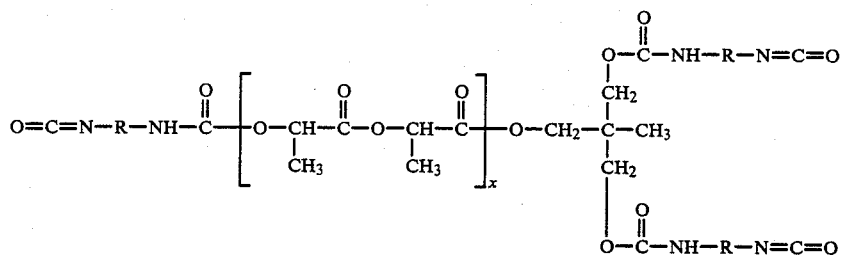
The aromatic diisoycanate may be toluene diisocyanate (TDI) or 4,4'-diphenylmethane diisocyanate (MDI).
Application of the resulting isocyanate-terminated prepolymer adhesive (1) to soft living tissue results in curing of the adhesive as follows:
REACTION SEQUENCE 3
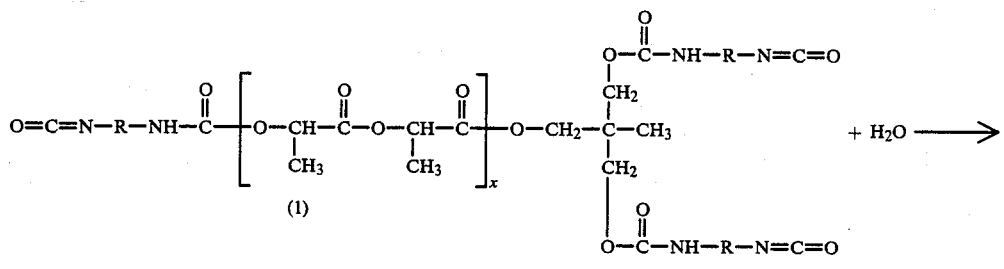 + $H_2O \longrightarrow$
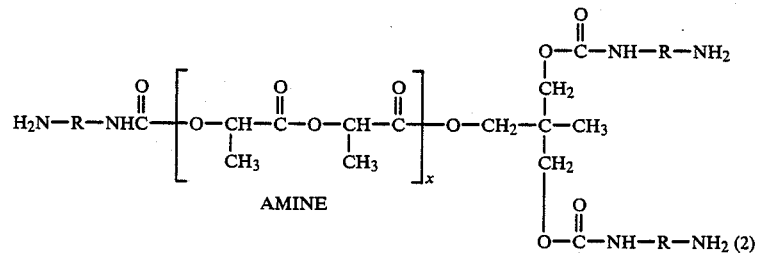 +
$3 CO_2$ 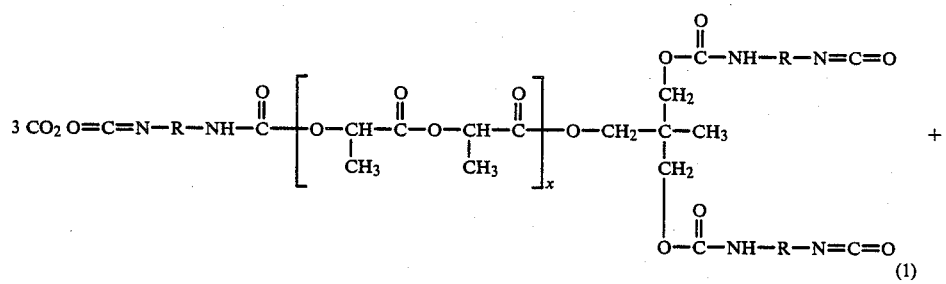 +
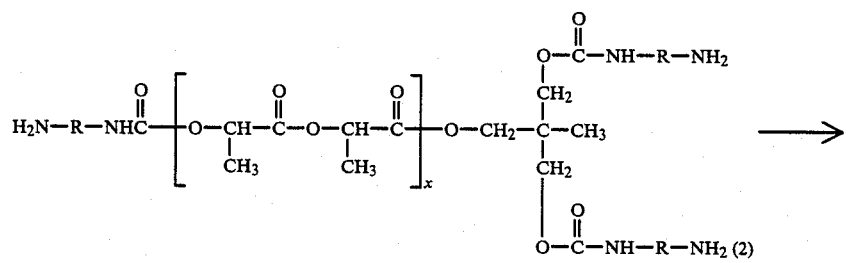 $\longrightarrow$

-continued
REACTION SEQUENCE 3

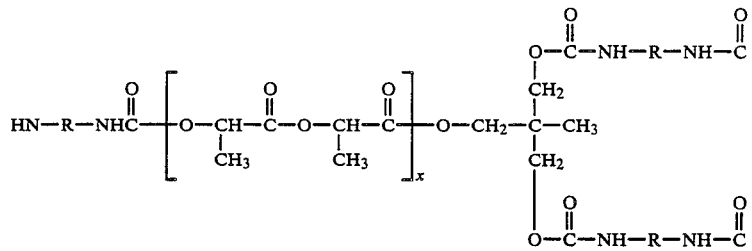

An isocyanate group reacts with water in the soft tissue to form $CO_2$ and an amine. The amine then reacts with another, as yet unhydrolyzed, isocyanate group to promote chain growth and cross linking through urea linkages.

It is believed that the binding of the tissue is primarily due to mechanical interlocking. The prepolymer adhesive is water soluble so the tissue is adequately wetted by this material. The wettability enables the material to seep into tissue crevices and provide good mechanical interlocking. The adhesive wets the microporous surface of the tissue and cures in place. It is also possible to obtain a reaction of the isocyanate groups with various reactive groups within the tissue such as amine, phenol or thiol and thereby have actual chemical bonding with the tissue as well as mechanical bonding. In addition, multiisocyanate functionality incorporated into the prepolymer adhesive ensures adequate crosslinking between prepolymer chains.

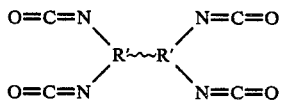

The resulting adhesive can be described as having a multifunctional resorbable backbone with diisocyanate endgroups which, when applied to the moist soft tissue, reacts with water to yield a cured adhesive having a resorbable backbone with urethane linkages. The backbone eventually dissolves by hydrolysis into biocompatable hydroxy acids which are normal metabolites. Lactic acid, for example, is used in the Krebs cycle. The tissue, by that time, has had an opportunity to undergo the normal regeneration process to heal the wound.

In the two-component system, the final step in the method of producing the adhesive is carried out just prior to use. Until that time, the components are separated, preferably by a barrier within a package employed to house the components until needed. The hydroxyl-terminated polyester obtained from reaction sequence 1 is combined with the excess diisocyanate just prior to application to the tissue. The reactions occurring at that time are the same as those shown in reaction sequence 2 and 3 except that they occur simultaneously. It is believed that the shelf-life of the two component system may be improved over that of the single component system.

In general, the single-component adhesive is prepared in the following way. The excess diisocyanate (approximately 6:1 mole ratio) is dissolved in an organic solvent, such as methylene chloride, and placed in a round-bottom flask. The polyester and 0.1 wt % catalyst are also dissolved in the same organic solvent. This solution is added slowly at room temperature to the diisocyanate solution. After the addition is complete, the resulting solution is stirred overnight at room temperature. The solvent is removed by using a rotary evaporator, and a viscous liquid is obtained which is applied with a pasteur pipet.

In general, the two-component adhesive is prepared by mixing aromatic diisocyanate, from 8 to 76 wt %, with the polyester, from 24 to 92 wt %. The adhesive is prepared in a dry $N_2$ atmosphere in a laboratory glove box at room temperature. First the appropriate amount of polyester is weighed into a beaker and then diluted with an organic solvent (40% based on total solids in adhesive). Catalyst (0.1 to 2%, based on weight of solids) is then added to the polyester solution and allowed to dissolve. The diisocyanate is then weighed into a separate beaker, and the polyester solution is added to it with rapid stirring. The adhesive can then be removed from the dry box and used by applying a few drops with a pasteur pipet.

Before curing, the adhesive is a clear to pale yellow, low-viscosity liquid that forms a white-foamed film when applied to animal tissue. The cured adhesive has an in vitro adhesive strength of 94 to 236 g/cm$^2$ and a set time of about 0.5 to 30 min.

Adhesives were prepared in the laboratory, and their adhesive strengths were evaluated in vitro using beef tissue. Although such testing only approximates the strength of the adhesive due to the potential for bias from the strength of the natural beef collagen fibers, a good initial idea of the adhesive ability of the material was obtained. Sets of fifteen 1.0-cu-in. blocks of beef muscle tissue were treated with the adhesives. The treated sets were held together with strings to ensure maximum contact of the surfaces and wrapped in polyethylene film to prevent dehydration. After curing for 2 hours, the bonding strengths were determined by pulling the samples apart using an Instron tensile tester. Comparisons were made to cyanoacrylate adhesives, a material known to be an effective tissue adhesive. In vitro strengths of some formulations were found to be superior to the cyanoacrylate adhesives. The formulations given in the footnotes follow the general scheme-theoretical molecular weight of prepolymer/initiator for poly(DL-lactide), wt % of polyester/type of diisocyanate, wt %/catalyst, wt %/solvent, wt % based on solids.

TABLE I
IN VITRO BONDING STRENGTH OF BIODEGRADABLE TISSUE ADHESIVES

| Formula No.* | Bonding Strength, g/cm$^2$ |
|---|---|
| 1 | 175 |
| 2 | 133 |
| 3 | 228 |

TABLE I-continued
IN VITRO BONDING STRENGTH OF BIODEGRADABLE TISSUE ADHESIVES

| Formula No.* | Bonding Strength, g/cm$^2$ |
| --- | --- |
| 4 | 196 |
| Cyanoacrylate Adhesive | 76 |

*Formula No.
1 5,000/THME,91/TDI,9/DABCO,0.05/CH$_2$Cl$_2$,40
2 5,000/PE,88/TDI,12/DABCO,0.1/CH$_2$Cl$_2$,40
3 10,000/THME,95/TDI,5/DABCO,0.03/CH$_2$Cl$_2$,40
4 10,000/THME,95/TDI,5/DABCO,0.1/CH$_2$Cl$_2$,40

Based on the in vitro bonding strength of the adhesive, animal studies were then undertaken using female Sprague-Dawley rats. Three parallel, longitudinal incisions were made through shaved skin over the dorsal anterior portion of the thorax of the rats. The left incision was closed with sutures, the middle incision was closed with the adhesive, and the right incision was closed with cyanoacrylate adhesive. The adhesives were formulated to adhere between 1 and 30 min. In some cases, animals reopened the wound sites of the experimental adhesive as well as the cyanoacrylate adhesive and the sutures by scratching at them. The experimental adhesives appeared to hold as well as the cyanoacrylate adhesive.

The following are some specific examples of adhesive formulations used in animal studies.

EXAMPLE 1
SINGLE COMPONENT SYSTEM

In this example, the single-component adhesive had the following composition, wt %.
Toluene diisocyanate, 63 wt %
Polyester composed of ethylene glycol-terminated 50:50 poly(DL-lactide)/ε-caprolactone, 37 wt %
Dibutyltin diacetate, 0.1 wt %

The adhesive was used to close incisions on the dorsal anterior portion of the thorax of rats. The incisions were closed with adhesive and held for 30 min. The incisions remained closed for three weeks, at which time the study was concluded. The in vitro tensile strength was 236 g/cm$^2$.

EXAMPLE 2
TWO COMPONENT SYSTEM

Examples of two-component adhesives are given in Table 1. Comparisons were made to cyanoacrylate adhesives. The formulations given in the footnotes follow the general scheme-theoretical molecular weight of prepolymer/initiator for poly(DL-lactide), wt % of polyester/type of diisocyanate, wt %/catalyst, wt %/solvent, wt % based on solids. Several observations can be made from the results of the studies. Although the first three adhesives were quite slow to cure, they all held successfully. In comparison, adhesives 4, 5 and 6 were faster to cure but in some cases failed to hold for the total testing period. Another factor contributing to the premature failure of some of the adhesives is the animals' scratching the incisions. This is evident from the fact that both the cyanoacrylate adhesive and sutures failed in many cases.

TABLE II
IN VIVO EFFICACY IN RATS OF TWO-COMPONENT ADHESIVES

| Animal No. | Formula No.* | In vivo adhesion time, min | Day test formula opened | Day cyanoacrylate adhesive opened | Day sutures failed | Week killed |
| --- | --- | --- | --- | --- | --- | --- |
| 1 | 1 | 5 | | | 5 | 1 |
| 2 | 2 | >5 | | | 2 | 1 |
| 3 | 2 | >5 | | | 8 | 3 |
| 4 | 3 | >5 | | | 3 | 3 |
| 5 | 3 | >5 | 1 | 5 | | 3 |
| 6 | 3 | >5 | | | 3 | 1 |
| 7 | 4 | 1 | 2 | | | 1 |
| 8 | 4 | 1 | 4 | 4 | 4 | 3 |
| 9 | 4 | 1 | 4 | 1 | | 2 |
| 10 | 5 | 2 | 8 | 4 | | 1 |
| 11 | 5 | 2 | 1 | | 8 | 3 |
| 12 | 5 | 2 | | | 8 | 2 |
| 13 | 6 | 6 | 4 | 4 | 9 | 2 |
| 14 | 6 | 6 | 1 | | | 1 |
| 15 | 6 | 3.5 | 8 | 4 | | 3 |

*Formula No.
1 10,000/THME,87/MDI,13/DABCO,0.1/CH$_2$Cl$_2$,40.
2 10,000/THME,92/TDI,8/DABCO,0.1/CH$_2$Cl$_2$,40.
3 5,000/PE,81/TDI,19/DABCO,0.1/Ethyl acetate, 40.
4 5,000/THME,85/TDI,15/DABCO,1.5/Ethyl acetate, 40.
5 5,000/THME,85/TDI,15/DABCO,1.0/Ethyl acetate, 40.
6 5,000/THME,85/TDI,15/DABCO,0.75/Ethyl acetate, 40.

What is claimed is:

1. A method of producing an adhesive for use in joining soft living tissues comprising the steps of:
   preparing a hydroxyl-terminated polyester by reacting a biodegradable monomer with a polyhydroxy polymerization initiator in the presence of a catalyst, wherein said monomer is selected from the group consisting of lactide, glycolide, ε-caprolactone and any combination thereof; and
   preparing a diisocyanate-terminated prepolymer adhesive by reacting said hydroxyl-terminated polyester with excess aromatic diisocyanate.

2. The method of claim 1 wherein said initiator is selected from the group consisting of ethylene glycol, diethylene glycol, 1,1,1-tris (hydroxymethyl) ethane and pentaerythritol.

3. The method of claim 1 wherein said catalyst is selected from the group consisting of stannous octoate, zinc compounds, aromatic and aliphatic tertiary amines, 1,4-diazabicyclo [2,2,2]octane and dibutyltin diacetate.

4. The method of claim 1 wherein said aromatic diisocyanate is selected from the group consisting of toluene diisocyanate and methylene-bis-phenyl diisocyanate.

5. The method of claim 1 wherein said catalyst is present in an amount up to about 2.0 weight percent.

6. The method of claim 1 wherein said aromatic diisocyanate is added in amounts from about 8 to 76 percent and said hydroxyl-terminated polyester is added in amounts from about 24 to 92 weight percent.

7. The method of claim 1 further comprising the step of applying said prepolymer adhesive to soft living tissue whereupon said prepolymer adhesive is hydrolyzed to promote chain growth and cross linking to effect bonding to said tissue.

8. The method of claim 1 wherein said diisocyanate and said polyester are separated by a barrier within a package until just prior to use whereupon said barrier is removed to permit reaction therebetween.

9. The method of claim 1 wherein said aromatic diisocyanate and said polyester are mixed in an organic solvent in a ratio of solids to solvent of about 60:40.

10. A method of producing an adhesive for use in joining soft living tissue comprising the steps of:
reacting a biodegradable monomer with a polyhydroxy polymerization initiator in the presence of a catalyst, wherein said monomer is selected from the group consisting of lactide, glycolide, ε-caprolactone and any combination thereof to yield a hydroxyl-terminated polyester;
dissolving said polyester and an additional effective amount of said catalyst in an organic solvent;
dissolving aromatic diisocyanate in a separate amount of said organic solvent;
stirring such polyester, catalyst, solvent mixture into such aromatic diisocyanate, solvent mixture; and
removing said solvent to yield a diisocyanate-terminated prepolymer adhesive.

11. The method of claim 10 further comprising the step of applying said prepolymer adhesive to soft living tissue whereupon said prepolymer adhesive is hydrolyzed to promote chain growth and cross linking through urea linkages to effect bonding to said tissue.

12. The method of claim 10 further comprising the steps of:
reacting said monomer with said initiator in the presence of said catalyst at about 140° C., stirring the mixture for about six hours, allowing the mixture to stand for about an additional twelve hours, cooling the mixture to room temperature and filtering the mixture to yield said polyester.

13. The method of claim 10 wherein said monomer is 50:50 DL-lactides/ε-caprolactone, said initiator is 1,1,1-tris (hydroxymethyl) ethane, said catalyst is stannous octoate, said aromatic diisocyanate is a multifunctional methyl-bis-phenyl diisocyanate and said organic solvent is ethyl acetate.

14. An adhesive for use in joining soft living tissues comprising:
a multifunctional resorbable polyester backbone having diisocyanate endgroups wherein said polyester backbone is selected from the group consisting of polymers and copolymers of lactide, glycolide and ε-caprolactone and has a theoretical molecular weight in the range of about 500 to 10,000.

15. The adhesive of claim 14 wherein said polyester backbone is 50:50 DL-lactide/ε-caprolactone.

16. The adhesive of claim 14 wherein said polyester backbone is poly(DL-lactide).

17. The adhesive of claim 14 wherein one end group of said polyester backbone is 1,1,1-tris (hydroxymethyl) ethane.

18. The adhesive of claim 14 wherein one end group of said polyester backbone is pentaerythritol.

19. The adhesive of claim 14 wherein one end group of said polyester backbone is ethylene glycol.

20. The adhesive of claim 14 wherein the in vitro tensile strength is in the range of about 94 to 236 g/cm$^2$.

21. The adhesive of claim 14 wherein the set time is in the range of a time up to about thirty minutes.

* * * * *

UNITED STATES PATENT AND TRADEMARK OFFICE
CERTIFICATE OF CORRECTION

PATENT NO. : 4,804,691

DATED : February 14, 1989

INVENTOR(S) : James P. English, et al.

It is certified that error appears in the above-identified patent and that said Letters Patent is hereby corrected as shown below:

Col. 2, line 30, after "ester" delete "monomermade" and substitute therefor --monomer made--.

Signed and Sealed this

Eighth Day of May, 1990

Attest:

HARRY F. MANBECK, JR.

*Attesting Officer*   *Commissioner of Patents and Trademarks*